(12) United States Patent
Watanabe et al.

(10) Patent No.: US 11,317,864 B2
(45) Date of Patent: May 3, 2022

(54) BIOMETRIC INFORMATION DETECTION DEVICE AND METHOD OF PRODUCING THE SAME, BIOMETRIC INFORMATION DETECTION MODULE AND METHOD OF PRODUCING THE SAME

(71) Applicants: SEIKO INSTRUMENTS INC., Chiba (JP); SHOWA UNIVERSITY, Tokyo (JP)

(72) Inventors: Shunji Watanabe, Chiba (JP); Yoshifumi Yoshida, Chiba (JP); Kotaro Maki, Tokyo (JP)

(73) Assignees: SEIKO HOLDINGS KABUSHIKI KAISHA, Tokyo (JP); SHOWA UNIVERSITY, Tokyo (JP)

( * ) Notice: Subject to any disclaimer, the term of this patent is extended or adjusted under 35 U.S.C. 154(b) by 367 days.

(21) Appl. No.: 16/384,029

(22) Filed: Apr. 15, 2019

(65) Prior Publication Data
US 2020/0029898 A1    Jan. 30, 2020

(30) Foreign Application Priority Data

Jul. 27, 2018 (JP) ............................. JP2018-141422

(51) Int. Cl.
*A61B 5/00* (2006.01)
*A61B 5/1455* (2006.01)
(Continued)

(52) U.S. Cl.
CPC .......... *A61B 5/682* (2013.01); *A61B 5/02433* (2013.01); *A61B 5/14532* (2013.01);
(Continued)

(58) Field of Classification Search
CPC . A61B 5/682; A61B 5/14551; A61B 5/14552; A61B 5/02433; A61B 5/14532;
(Continued)

(56) References Cited

U.S. PATENT DOCUMENTS 6,470,200 B2 * 10/2002 Walker ............... A61B 5/14552
600/344
8,771,149 B2    7/2014 Rahman et al.
(Continued)

FOREIGN PATENT DOCUMENTS

JP    2004-167120 A    6/2004

OTHER PUBLICATIONS

Extended European Search Report in Europe Application No. 19169159.1, dated Oct. 29, 2019, 8 pages.

*Primary Examiner* — Chu Chuan Liu
(74) *Attorney, Agent, or Firm* — Crowell & Moring LLP

(57) ABSTRACT

A biometric information detection device according to one embodiment of the present disclosure is configured to be installed in a living body, and includes a sensor, a battery, a mechanical switch, a sealing member, and a holding member. The mechanical switch switches between a conduction state in which power is supplied from the battery to the sensor and a cutoff state in which supply of the power is blocked. The sealing member seals all of the sensor, the battery, and the mechanical switch. The holding member is attached to the living body and holds the sealing member.

17 Claims, 9 Drawing Sheets

(51) Int. Cl.
  *A61B 5/024* (2006.01)
  *A61B 5/145* (2006.01)
(52) U.S. Cl.
  CPC .. *A61B 5/14552* (2013.01); *A61B 2560/0214* (2013.01); *A61B 2562/0238* (2013.01)
(58) Field of Classification Search
  CPC . A61B 5/4552; A61B 5/6835; A61B 5/02141; A61B 5/02427; A61B 5/02438; A61B 5/02108; A61B 5/228; A61B 5/0088; A61B 5/4547; A61B 2560/0214; A61B 2560/0209
  See application file for complete search history.

(56) References Cited

U.S. PATENT DOCUMENTS

| | | | |
|---|---|---|---|
| 9,795,296 B2* | 10/2017 | Imran | A61B 5/0816 |
| 2004/0267166 A1 | 12/2004 | Ooshima et al. | |
| 2009/0210032 A1* | 8/2009 | Beiski | A61N 1/0548 607/59 |
| 2018/0000563 A1 | 1/2018 | Shanjani et al. | |

* cited by examiner

BIOMETRIC INFORMATION DETECTION DEVICE AND METHOD OF PRODUCING THE SAME, BIOMETRIC INFORMATION DETECTION MODULE AND METHOD OF PRODUCING THE SAME

RELATED APPLICATIONS

Priority is claimed on Japanese Patent Application No. 2018-141422, filed on Jul. 27, 2018, the content of which is incorporated herein by reference.

BACKGROUND OF THE INVENTION

1. Field of the Invention

The present disclosure relates to a biometric information detection module configured to detect biometric information of a subject, a biometric information detection device including the same, and method of producing the same.

2. Description of the Related Art

Several biological monitors that are installed in the oral cavity to obtain biometric information have been proposed so far (for example, refer to Patent Documents 1 and 2).

PATENT DOCUMENTS

[Patent Document 1] Japanese Unexamined Patent Application, First Publication No. 2004-167120
[Patent Document 2] U.S. Pat. No. 8,771,149

SUMMARY OF THE INVENTION

In such devices, it is desirable to secure high safety and maintain an accurate operation for a long time. Therefore, it is desirable to provide a biometric information detection module and a biometric information detection device having excellent safety and long-term reliability, and a method of producing the same.

A biometric information detection device according to one embodiment of the present disclosure is configured to be installed in a living body, and includes a sensor, a battery, a mechanical switch, a sealing member, and a holding member. The mechanical switch switches between a conduction state in which power is supplied from the battery to the sensor and a cutoff state in which supply of the power from the battery to the sensor is blocked. The sealing member seals all of the sensor, the battery, and the mechanical switch. The holding member is configured to be attached to the living body and holds the sealing member.

According to the biometric information detection device of one embodiment of the present disclosure, since the sensor, the battery, and the mechanical switch are sealed with the sealing member, it is possible to secure both high waterproofness with respect to the sensor and the like and high safety for a living body. In addition, the mechanical switch can switch between a conduction state and a cutoff state, which contributes to prolonging the lifespan of the battery. Thereby, excellent long-term reliability is obtained.

DETAILED DESCRIPTION OF THE PREFERRED EMBODIMENTS

Embodiments of the present disclosure will be described below in detail with reference to the drawings. Here, the description will be made in the following order.

1. Embodiment (Example of Mouthpiece-Like Biometric Information Detection Device in which a Light Sensor That Receives Reflected Light From the Gums is Sealed)

2. Modified Examples

Modified Example 1 (example of a biometric information detection module in which an operation unit of a mechanical switch is protected by folding back a sealing area of a laminate film type battery)

Modified Example 2 (example of a biometric information detection device in which a protective part protruding from an operation unit is provided in a main body of a mechanical switch)

Modified Example 3 (example of a biometric information detection device in which a sealing member and a holding member are constituted by separate members)

Modified Example 4 (example of a biometric information detection device that receives reflected light from parts other than the gum)

Modified Example 5 (example of a biometric information detection device having a strain sensor)

Modified Example 6 (example of a biometric information detection device having an acceleration sensor)

3. Other Modified Examples

1. Embodiment

Overall Configuration of Biometric Information Detection Device 1

Figure 1:
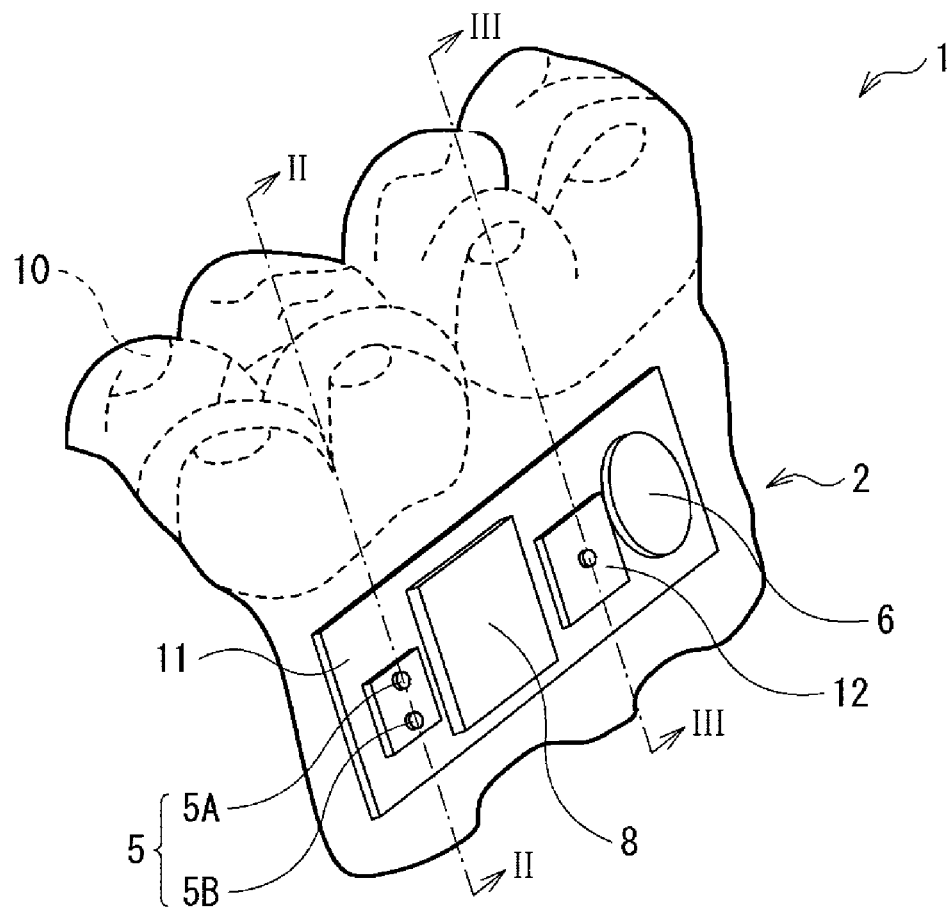
FIG. 1 is a perspective view showing an appearance of a biometric information detection device according to one embodiment of the present disclosure.

FIG. 1 is a schematic perspective view of a schematic configuration example of a biometric information detection device 1 according to one embodiment of the present disclosure. In addition, both FIG. 2 and FIG. 3 show a schematic cross-sectional view of a schematic configuration example of the biometric information detection device 1.

Figure 2:
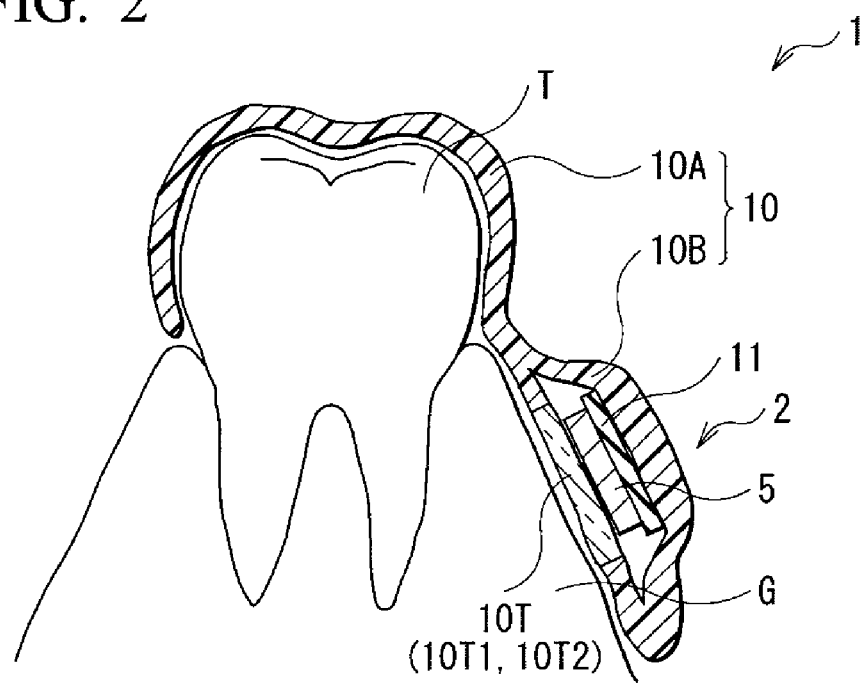
FIG. 2 is a cross-sectional view showing a schematic cross-sectional configuration example of the biometric information detection device shown in FIG. 1.
Figure 3:
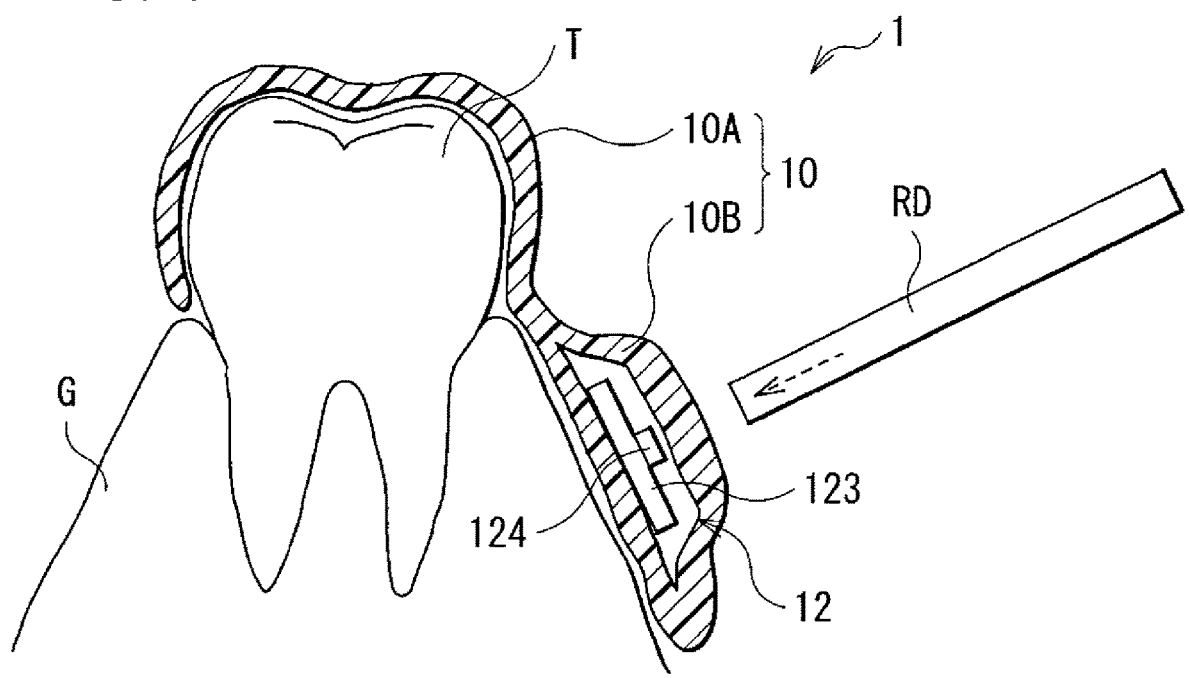
FIG. 3 is another cross-sectional view showing a schematic cross-sectional configuration example of the biometric information detection device shown in FIG. 1.
Figure 4:
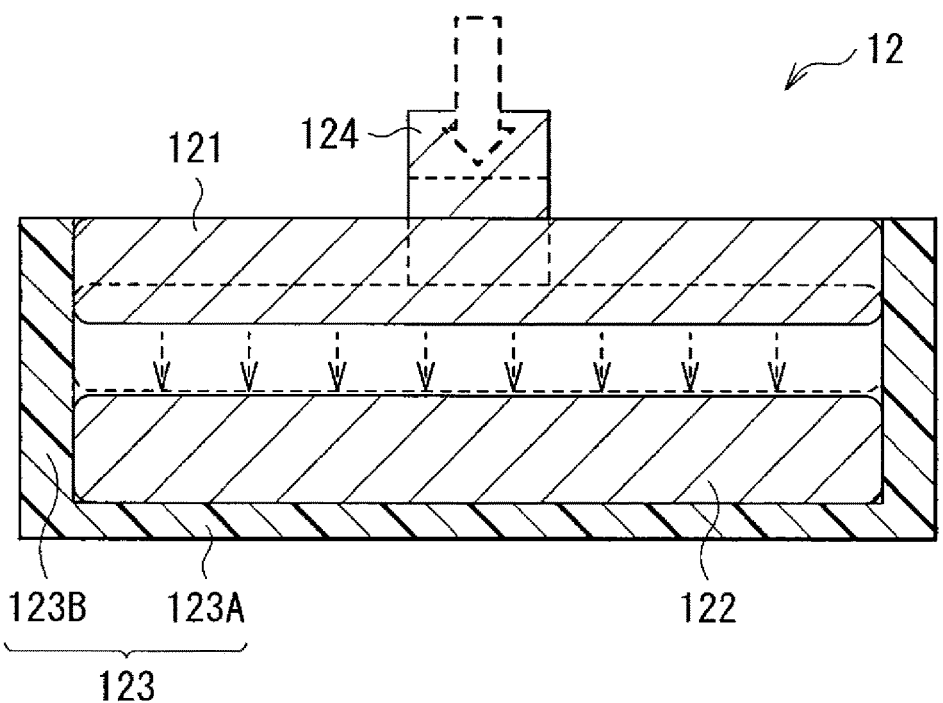
FIG. 4 is a cross-sectional view showing a schematic configuration example of a mechanical switch shown in FIG. 3.
Figure 5:
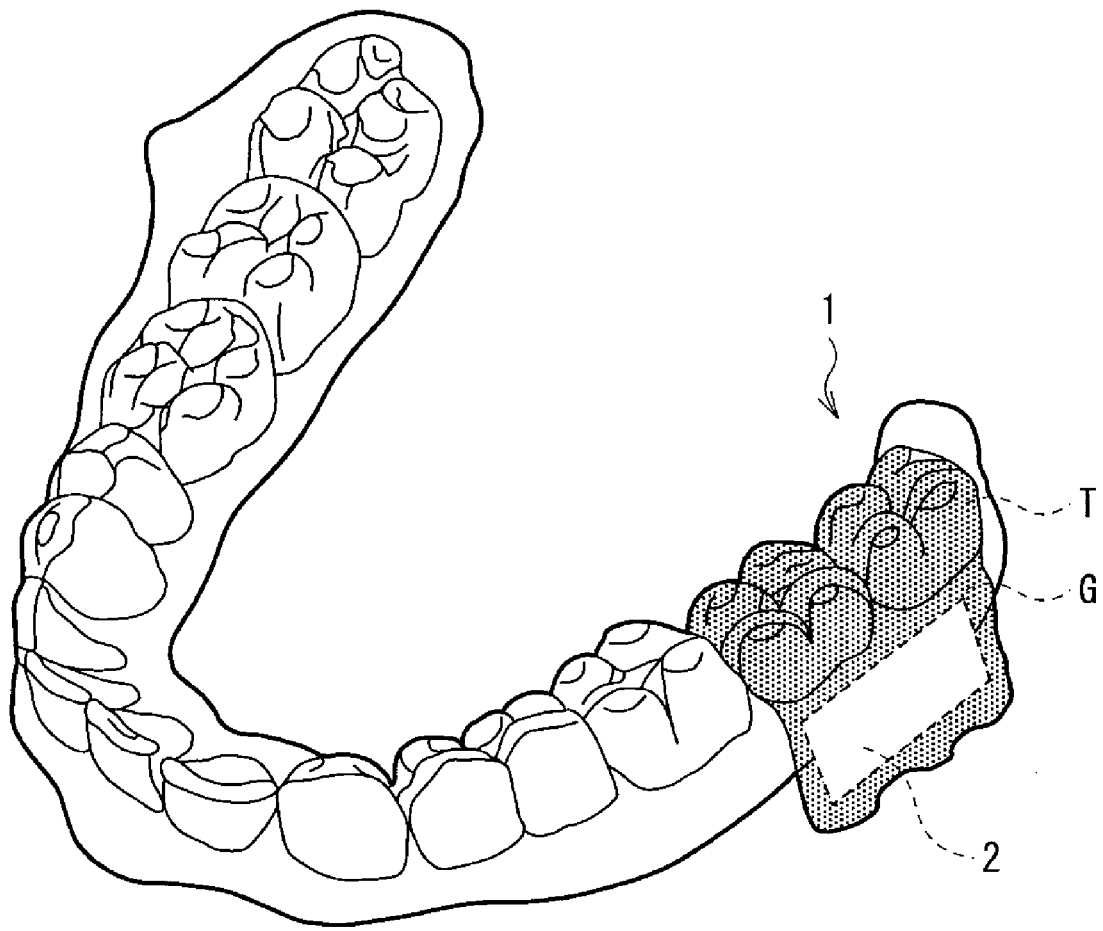
FIG. 5 is a perspective view showing an example in which the biometric information detection device shown in FIG. 1 is installed in the oral cavity.
Figure 6:
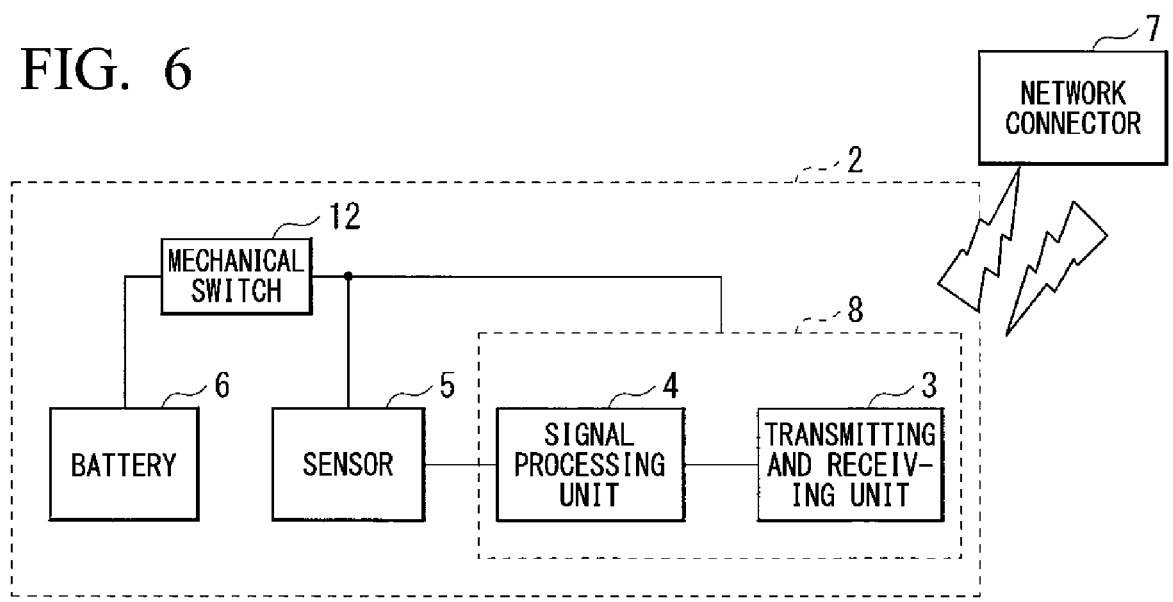
FIG. 6 is a block diagram showing an overall configuration example of the biometric information detection device shown in FIG. 1.

Here, FIG. 2 shows a cross section including a light sensor 5 (to be described below in detail) shown in FIG. 1. FIG. 3 shows a cross section including a mechanical switch 12 (to be described below in detail) shown in FIG. 1. FIG. 2 shows a cross section taken along the line II-II shown in FIG. 1 in an arrow direction. FIG. 3 shows a cross section taken along the line III-III shown in FIG. 1 in an arrow direction. In addition, FIG. 4 is an enlarged cross-sectional view of the mechanical switch 12. In addition, FIG. 5 is a perspective view showing an example of a use state of the biometric information detection device 1. In addition, FIG. 6 is a block diagram showing a configuration of a biometric information detection module 2 included in the biometric information detection device 1.

As shown in FIG. 5, the biometric information detection device 1 is installed in a living body, for example, in the oral cavity, and more specifically, is installed so that it covers a part of teeth T and a part of the gums G.

A shown in FIG. 1, the biometric information detection device 1 includes a shell 10 that covers the teeth T and the gums G, and the biometric information detection module 2 built into the shell 10.

As shown in FIG. 2 and FIG. 3, the shell 10 has a has a mouthpiece shape in which an upper part 10A covering the teeth T and a lower part 10B covering the gums G are integrated, and is made of, for example, a thermoplastic polymer compound. As the thermoplastic polymer compound, for example, compounds including polyethylene, polyurethane, acrylic or the like, can be applied. The biometric information detection module 2 is embedded in the lower part 10B so that it is sealed from the outside. Therefore, the lower part 10B of the shell 10 is one specific example corresponding to a "sealing member" of the present disclosure. In this manner, since the biometric information detection module 2 is embedded in the lower part 10B of the shell 10, it is reliably guarded from saliva in the oral cavity, water from drinks and the like, and outside air. In addition, since the upper part 10A of the shell 10 is integrated with the lower part 10B, it corresponds to one specific example of a "holding member" of the present disclosure which holds the lower part 10B as a sealing member in the oral cavity. Here, for the convenience of explanation, FIG. 1 shows a state in which a part of the shell 10 covering the biometric information detection module 2 is removed in order to improve the visibility. However, actually, since the biometric information detection module 2 is covered with the shell 10, it is not visible from the outside unless the shell 10 is transparent.

In the biometric information detection module 2, for example, a battery 6, the mechanical switch 12, a transmitting and receiving module 8, and the light sensor 5 are disposed on a mounting board 11 (refer to FIGS. 1, 2, and 6).

The mounting board 11 is, for example, a sheet-like flexible board on which a wiring is printed.

The battery 6 functions as a power supply configured to supply power for driving the light sensor 5 and the transmitting and receiving module 8, to the light sensor 5 and the transmitting and receiving module 8. The battery 6 is, for example, a button type or coin type primary battery. Alternatively, as the battery 6, a secondary battery may be applied as long as it can perform non-contact charging. In addition, the structure of the battery 6 is not particularly limited, and a laminate in which a positive electrode and a negative electrode are alternatively laminated with an electrolyte therebetween may be housed in a housing made of a metal or the like for an electrode structure, or additionally a wound structure in which the laminate is wound may be housed in a housing for an electrode structure.

For example, the mechanical switch 12 is disposed between the battery 6 and the transmitting and receiving module 8 on the mounting board 11, and turns supply of power from the battery 6 to the light sensor 5 and the transmitting and receiving module 8 on or off. The mechanical switch 12 is a so-called alternate type self-holding type switch. As shown in FIG. 4, the mechanical switch 12 includes a main body 123 in which a first conductor 121 and a second conductor 122 are housed, and an operation unit 124. The main body 123 is a housing in which the first conductor 121 and the second conductor 122 are housed, and includes a bottom part 123A and a wall part 123B which stands along the circumference of the bottom part 123A and surrounds the first conductor 121 and the second conductor 122. In the mechanical switch 12, when the operation unit 124 is operated, contact and separation between the first conductor 121 and the second conductor 122 are repeated inside the main body 123. For example, the operation unit 124 is fixed to the first conductor 121, and performs a contact operation of bringing the first conductor 121 into contact with the second conductor 122 and a separation operation of separating the first conductor 121 from the second conductor 122. As shown in FIG. 3, when a user pushes and releases the operation unit 124 once using, for example, an operation rod RD, a contact operation between the first conductor 121 and the second conductor 122 is performed and an on state is brought about. In addition, when the user pushes and releases the operation unit 124 once using an operation rod RD or the like, a separation operation between the first conductor 121 and the second conductor 122 is performed and an off state is brought about. Here, FIG. 4 shows an example in which the second conductor 122 is fixed to the main body 123, and the first conductor 121 is displaceable relative to the second conductor 122. In FIG. 4, the first conductor 121 in an on state is indicated by a dashed line and the first conductor 121 in an off state is indicated by a solid line.

As shown in FIG. 6, the transmitting and receiving module 8 includes, for example a transmitting and receiving unit 3 and a signal processing unit 4. Generally, chips in which the transmitting and receiving unit 3 and the signal processing unit 4 are integrated are distributed. The transmitting and receiving unit 3 is an antenna that performs wireless type data communication with a network connector 7 provided outside the biometric information detection module 2. Here, the network connector 7 is a communication device, for example, a personal computer, a tablet terminal, or a smartphone, that can be connected to a network such as the Internet. In addition, the signal processing unit 4 is, for example, a signal processing circuit including a memory, a microprocessor, an analog-to-digital (A/D) converter, and the like. A detection signal (output signal) from the light sensor 5 is input to the signal processing unit 4. The signal processing unit 4 is driven by receiving supply of power from the battery 6, and generates a digital data signal that can be transmitted through the transmitting and receiving unit 3, based on the output signal from the light sensor 5. The transmitting and receiving unit 3 is driven by receiving supply of power from the battery 6, and can transmit the digital data signal wirelessly from the signal processing unit 4 to an external network through the network connector 7. In addition, the transmitting and receiving unit 3 can receive a control signal wirelessly from the external network through the network connector 7. Here, in FIG. 1 and the like, the mounting board 11 has a rectangular planar shape, and the battery 6, the transmitting and receiving module 8, and the light sensor 5 are disposed in a row. However, the present disclosure is not limited thereto, and the layout of the battery 6, the transmitting and receiving module 8 and the light sensor 5 can be arbitrarily set.

The light sensor 5 is, for example, a reflective photoelectric sensor, and includes a light emitting element 5A that can emit light such as a light emitting diode and a light receiving element 5B that can receive light emitted from the light emitting element 5A such as a photodiode. Light emitted from the light emitting element 5A has, for example, a wavelength of 400 nm or more and 1,000 nm or less. A part of the lower part 10B of the shell 10 covering the biometric information detection module 2, which covers the light emitting element 5A, is a first light-transmitting part 10T1 that can transmit light emitted from the light emitting element 5A (refer to FIG. 2). In addition, a part of the lower part 10B of the shell 10, which covers the light receiving element 5B, is a second light-transmitting part 10T2 that can transmit light that is reflected from the inside of the gums G or the vicinity of the surface of the gums G from light emitted from the light emitting element 5A (refer to FIG. 2). The first light-transmitting part 10T1 and the second light-transmitting part 10T2 may also be made of a thermoplastic polymer compound. Here, a constituent material of the first light-transmitting part 10T1 and a constituent material of the second light-transmitting part 10T2 may be substantially the same material, and, they may be constituted using, for example, a transparent material among the above-described thermoplastic polymer compounds. In addition, the first light-transmitting part 10T1 and the second light-transmitting part 10T2 need not be separated, and may be continuously formed. This is advantageous for integrated formation. In addition, the entire lower part 10B may be transparent, and the entire shell 10 in which the upper part 10A is incorporated into the lower part 10B may be transparent. That is, in the shell 10, the first light-transmitting part 10T1 covering the light emitting element 5A and the second light-transmitting part 10T2 covering the light receiving element 5B (these are collectively referred to as the light-transmitting part 10T) may have light transmitting properties, and parts other than the light-transmitting part 10T may have light shielding properties or light transmitting properties.

Figure 7:
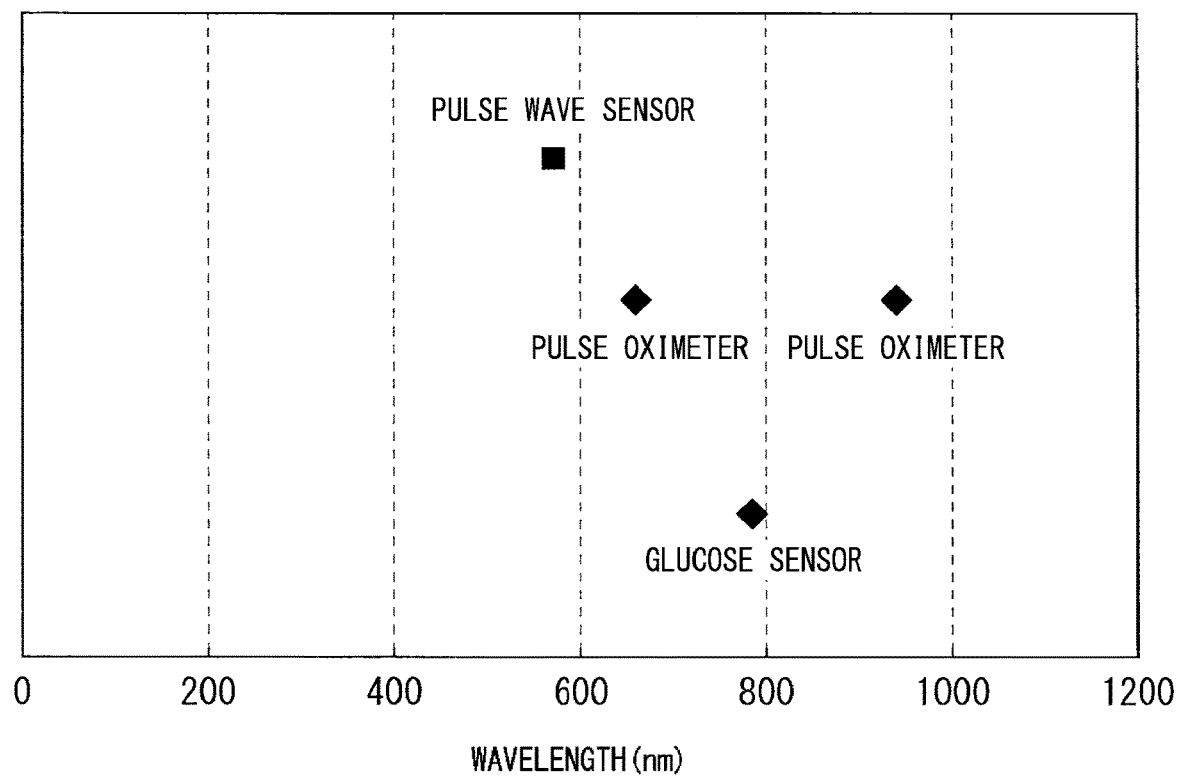
FIG. 7 is a characteristic diagram showing light receiving wavelength ranges of devices that can be applied to a light receiving element of a light sensor shown in FIG. 1.

The light emitting element 5A is disposed to face the gums G with the first light-transmitting part 10T1 therebetween. The light receiving element 5B is disposed near the light emitting element 5A so that it faces the gums G with the second light-transmitting part 10T2 therebetween. Therefore, light emitted from the light emitting element 5A passes through the first light-transmitting part 10T1 of the shell 10, reaches the gums G, and is reflected at the gums G. Light reflected from the gums G passes through the second light-transmitting part 10T2 of the shell 10 and enters the light receiving element 5B. Reflected light incident on the light receiving element 5B includes, for example, biometric information such as a blood flow rate. The light sensor 5 is, for example, a pulse wave sensor configured to detect a pulse wave using the above biometric information, a pulse oximeter configured to detect percutaneous arterial oxygen saturation ($SpO_2$) and a pulse rate using the above biometric information, or a glucose sensor configured to detect a glucose concentration using the above biometric information. Here, the light receiving element 5B of the light sensor 5 has different light receiving wavelength ranges according to types of biometric information to be acquired. FIG. 7 shows light receiving wavelength ranges in devices suitable for acquiring various types of biometric information. As shown in FIG. 7, the light receiving element 5B that can receive light with a wavelength of about 570 nm is used for the pulse wave sensor, the light receiving element 5B that can receive light with a wavelength of about 600 nm to 1,000 nm is used for the pulse oximeter configured to measure percutaneous arterial oxygen saturation, and the light receiving element 5B that can receive light with a wavelength of about 750 nm is used for a glucose sensor configured to detect a glucose concentration.

Method of Producing Biometric Information Detection Device 1

Figure 8A:
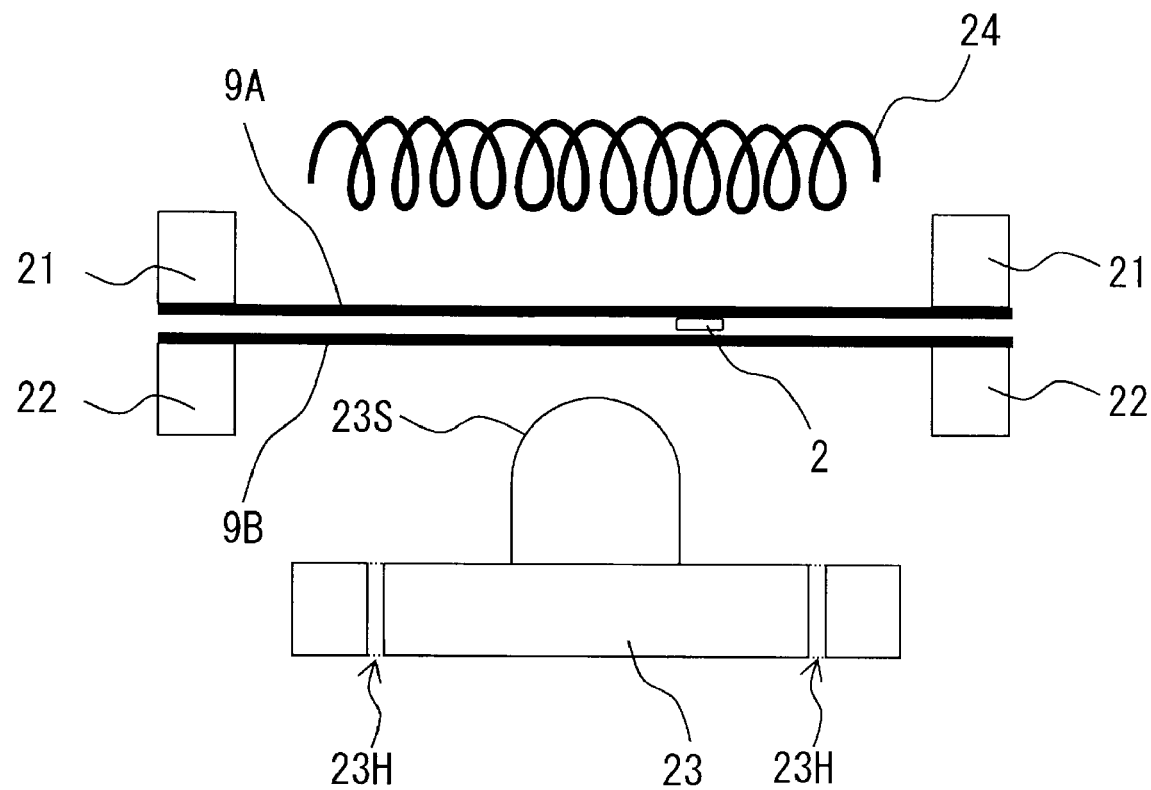
FIG. 8A is an explanatory diagram showing one process of a method of producing a biometric information detection device shown in FIG. 1.
Figure 8B:
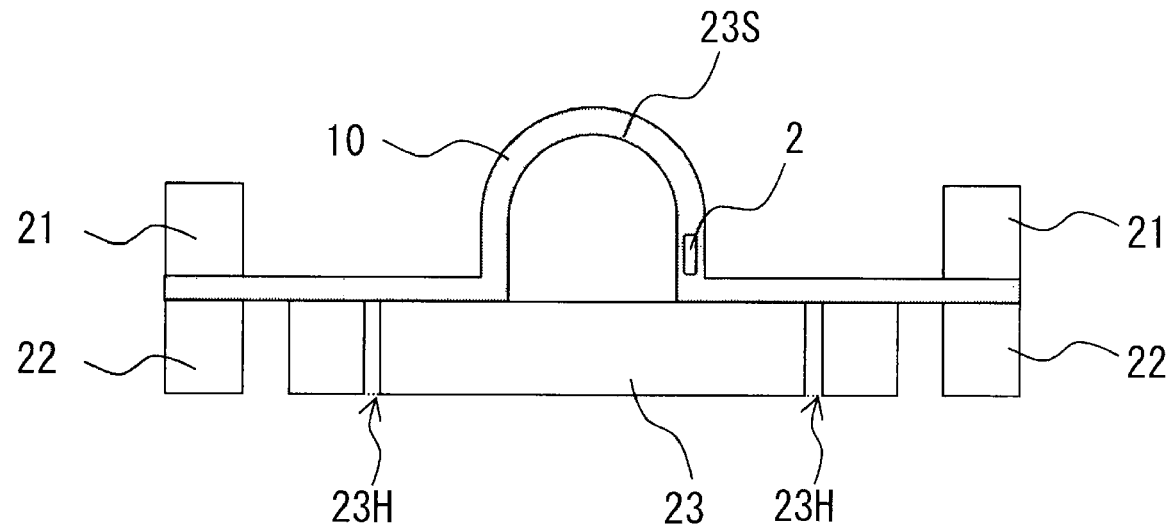
FIG. 8B is an explanatory diagram showing one process following FIG. 8A.

Next, a method of producing the biometric information detection device 1 will be described with reference to FIG. 8A and FIG. 8B in addition to FIG. 1 to FIG. 7. FIG. 8A is an explanatory diagram showing one process of the method of producing the biometric information detection device 1, and FIG. 8B is an explanatory diagram showing one process following FIG. 8A. Here, FIG. 8A and FIG. 8B are schematic diagrams showing only main members related to the explanation of this production process.

In order to produce the biometric information detection device 1, first, the above biometric information detection module 2 is prepared. Next, for example, as shown in FIG. 8A, the biometric information detection module 2 is placed between two sealing films 9A and 9B made of a thermoplastic polymer compound. Here, the sealing film 9A is held by a holding member 21 and the sealing film 9B is held by the holding member 21. Meanwhile, a tooth form 23 matching the teeth T and the gums G of a user who will wear the biometric information detection device 1 is prepared. The tooth form 23 can be molded by, for example, stamping or a 3D printer. Then, a part of the sealing films 9A and 9B in the vicinity of the light sensor 5 is heated to a temperature of about 280° C. by a heater 24, and as shown in FIG. 8B, the tooth form 23 is pressed against the sealing films 9A and 9B and subjected to molding. Here, a heating temperature of the heater 24 is not limited to the above 280° C., and it can be arbitrarily set, for example, within a range of 100° C. to 300° C. During molding, when air in the gap between the tooth form 23 and the sealing films 9A and 9B is discharged from a through-hole 23H of the tooth form 23, a surface 23S of the tooth form 23 and the sealing films 9A and 9B are brought into close contact with each other. Therefore, the sealing films 9A and 9B are deformed into a shape conforming to the surface 23S of the tooth form 23 and welded. Then, when the tooth form 23 and the welded sealing films 9A and 9B are cooled, the mouthpiece-like shell 10 in which the upper part 10A and the lower part 10B are integrated is obtained. When the shell 10 is separated from the tooth form 23, the biometric information detection device 1 is obtained. In this manner, since the shell 10 in which the lower part 10B as a sealing member and the upper part 10A as a holding member are integrated is integrally formed by molding, it is possible to efficiently produce the biometric information detection device 1. Here, in FIG. 8A and FIG. 8B, the tooth form 23 having the surface 23S with a very simplified shape is shown. However, actually, the surface 23S of the tooth form 23 has a unique shape according to each user.

Actions and Effects

In this manner, according to the biometric information detection device 1 of the present embodiment, the mechanical switch 12 is provided in the biometric information detection module 2, and switches between a conduction state in which power is supplied from the battery 6 to the light sensor 5 and the transmitting and receiving module 8 and a cutoff state in which supply of the power is blocked. Therefore, the mechanical switch 12 is turned on, and power is supplied to the light sensor 5 and the transmitting and receiving module 8 only when it is desired to detect biometric information, and thus it is not necessary to constantly supply power. Therefore, it is possible to reduce power consumption, and if the battery 6 is a primary battery, it is possible to prolong the lifespan of the battery 6, and if the battery 6 is a secondary battery, it is possible to lower a charging frequency. Alternatively, since a battery capacity of the battery 6 can be reduced, it is possible to reduce the size of the battery 6, and thus it is possible to reduce the sizes of the biometric information detection module 2 and the biometric information detection device 1 themselves. Incidentally, also in the related art, for example, as disclosed in the above Patent Document 1 and Patent Document 2, detection of biometric information using a sensor installed in the oral cavity has been attempted. However, since a biometric information detection module of the related art does not have a power on and off switch, consumption of battery power starts from when the battery, the transmitting and receiving module, and the like are connected. Therefore, there is a risk of biometric information not being detected in stages of actual use, for example, when it is used for a long time, after it is produced, and when a long period has elapsed. In this regard, according to the biometric information detection device 1 of the present embodiment, since the mechanical switch 12 is provided in the biometric information detection module 2 as described above, and a current can be applied only when it is used, actual use is possible for a long time.

In the related art, for example, as disclosed in the above Patent Document 1 and Patent Document 2, attempts to detect biometric information using a sensor installed in the oral cavity have been made. However, a part of a sensor in a sensor module or the entire sensor, or some of other constituent members in a sensor module or all of the other constituent members are exposed in the oral cavity. Thus, there is a concern of an influence on a living body and it is thought that deterioration of the sensor and deterioration of the sensor module are likely to occur. On the other hand, according to the biometric information detection module 2 and the biometric information detection device 1, since the light sensor 5 is sealed with the shell 10 as a sealing member, high waterproofness and high safety are secured. Therefore, the biometric information detection module 2 and the biometric information detection device 1 have superior long-term reliability to that of biometric information detection modules of the related art.

In addition, according to the biometric information detection device 1, the light sensor 5 acquires an output signal including biometric information and the output signal is transmitted from the transmitting and receiving unit 3 to the network connector 7 through the signal processing unit 4, and can be additionally transmitted to an external network. When this output signal is analyzed, it is possible to obtain specific biometric information due to a disease of a patient who is a user to whom the biometric information detection device 1 is attached. In addition, it is possible to recognize change in daily health conditions in healthy users and maintain and manage health conditions. These information items can be very useful information for users themselves or doctors in charge thereof.

In addition, in the biometric information detection module 2 and the biometric information detection device 1, in the lower part 10B of the shell 10, the first light-transmitting part 10T1 and the second light-transmitting part 10T2 are provided and emit light outside of the lower part 10B of the shell 10 and receive light from the outside. Therefore, the light sensor 5 can obtain biometric information from, for example, the teeth T and the gums G with high accuracy even if it is sealed with the shell 10. On the other hand, it is thought that, in a sensor module of the related art, since it is necessary to expose a sensor in the oral cavity, deterioration such as corrosion of the sensor itself is likely to occur. In the sensor module of the related art, even if only a terminal part of a sensor is exposed in the oral cavity and the other part is molded with a resin or the like, this is insufficient in consideration of long-term reliability because a possibility of water entering from an interface between the exposed part and the molded part still remains.

Since the light sensor 5 is held by the upper part 10A via the lower part 10B, relative positions between the light sensor 5, and the teeth T and the gums G are stable, and improvement in detection accuracy can be expected.

In addition, in the light sensor 5, light is emitted to the gums G from the light emitting element 5A disposed to face the gums G, and light reflected from the gums G is detected by the light receiving element 5B disposed to face the gums G. Therefore, for example, compared with the case in which light is emitted to the skin outside the oral cavity and reflected light is detected, biometric information with higher accuracy is obtained. In addition, since the biometric information detection module 2 is always disposed in the oral cavity in a relatively stable temperature environment, biometric information with higher accuracy is obtained compared with the case in which the biometric information detection module 2 is attached outside the oral cavity, for example, to the arms and fingers.

2. Modified Examples

Next, modified examples (Modified Examples 1 to 6) of the above embodiment will be described. Here, components the same as those in the embodiment will be denoted with the same reference numerals and descriptions thereof will be appropriately omitted.

Modified Example 1

Figure 9A:
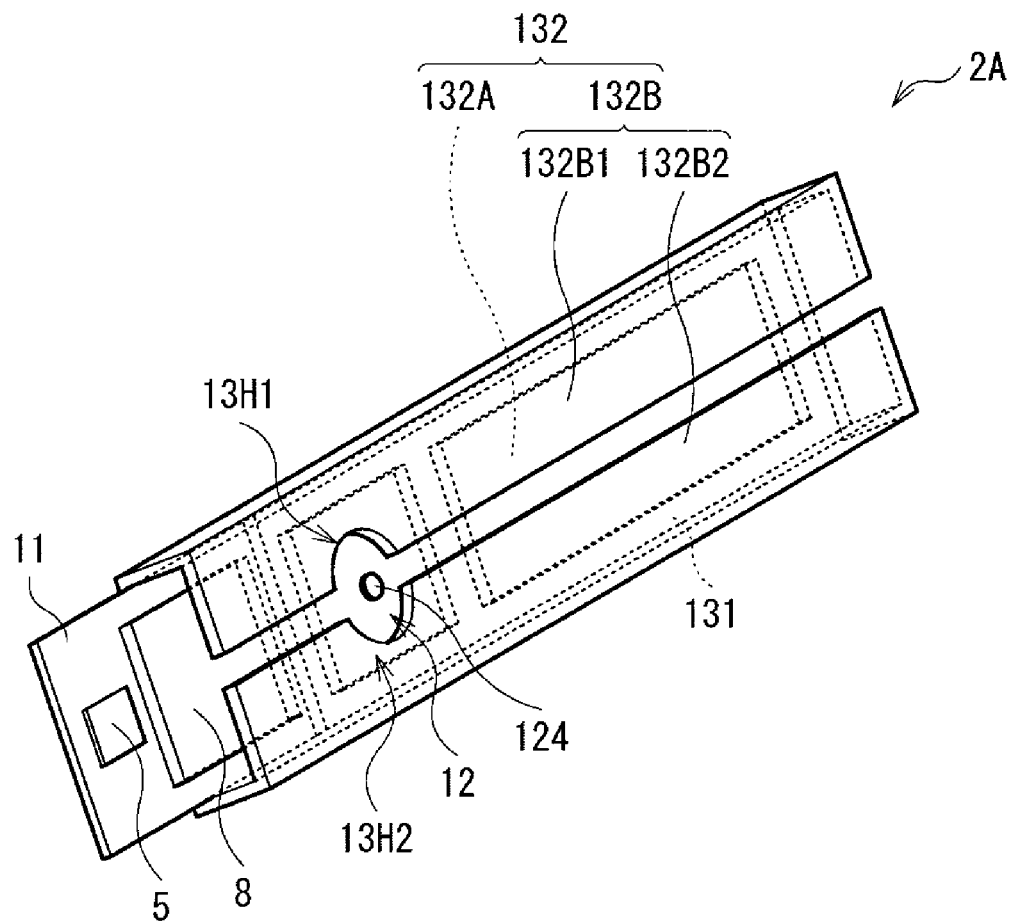
FIG. 9A is a perspective view showing a schematic configuration example of a biometric information detection module as Modified Example 1 of the present disclosure.
Figure 9B:
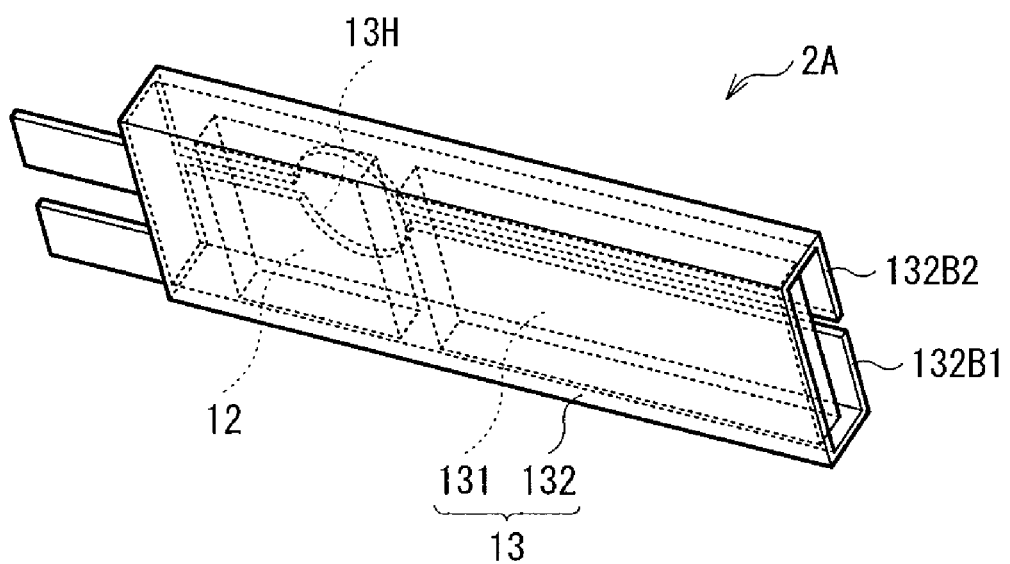
FIG. 9B is another perspective view showing a schematic configuration example of the biometric information detection module shown in FIG. 9A.

While the battery 6 with an electrode structure that is housed in a housing made of a metal or like has been exemplified in the biometric information detection module 2 of the biometric information detection device 1 of the above embodiment, the present disclosure is not limited thereto. For example, as in the biometric information detection module 2A as a first modified example (Modified Example 1) of the present disclosure shown in FIG. 9A and FIG. 9B, a battery 13 having excellent flexibility may be included. FIG. 9A is a perspective view of the biometric information detection module 2A when viewed from the front. FIG. 9B is a perspective view of the biometric information detection module 2A when viewed from the rear.

As shown in FIG. 9A and FIG. 9B, the battery 13 includes an electrode structure 131 and an exterior member 132 enclosing the electrode structure 131. For example, the electrode structure 131 is a laminate in which a positive electrode and a negative electrode are alternatively laminated with an electrolyte therebetween. For example, the exterior member 132 is obtained by welding two laminated films in which a metal foil and a laminate film are adhered and has high flexibility. The exterior member 132 includes a main body area 132A covering the electrode structure 131 and a sealing area 132B protruding from the main body area 132A. In the sealing area 132B, the mounting board 11 on which the light sensor 5, the transmitting and receiving module 8, and the mechanical switch 12 are disposed is placed. Here, in FIG. 9B, the mounting board 11, the light sensor 5, and the transmitting and receiving module 8 are not shown. In addition, the mounting board 11 may be provided in the main body area 132A. The sealing area 132B is a welding margin when two laminated films are bonded to each other, and surrounds at least a part of the mechanical switch 12. More specifically, the sealing area 132B of the exterior member 132 is folded back so that it covers the mounting board 11, and has eaves parts 132B1 and 132B2 that are positioned on the side opposite to the main body area 132A of the exterior member 132 when viewed from the operation unit 124. The eaves parts 132B1 and 132B2 have substantially semicircular notches 13H1 and 13H2 that are provided at positions corresponding to the operation unit 124. Here, in FIG. 9A and FIG. 9B, the pair of notches 13H1 and 13H2 are separated from and facing each other, and form a substantially circular opening. However, the eaves part 132B1 and the eaves part 132B2 may be adhered to each other, and the pair of notches 13H1 and 13H2 may be integrated to form a circular opening.

In the biometric information detection module 2A of this modified example, when an area corresponding to the opening formed by the pair of the notches 13H1 and 13H2 is pressed from above the lower part 10B of the shell 10 covering the biometric information detection module 2 using an operation rod RD (refer to FIG. 3), the operation unit 124 of the mechanical switch 12 can be operated. In addition, it is practically difficult to operate the operation unit 124 of the mechanical switch 12 unless such a rod-like tool is used. That is, the eaves parts 132B1 and 132B2 are protective members for protection from an inadvertent operation. Therefore, according to the biometric information detection module 2A of this modified example, it is possible to reduce a likelihood of malfunction and it is possible to obtain higher operation reliability.

Modified Example 2

Figure 10A:
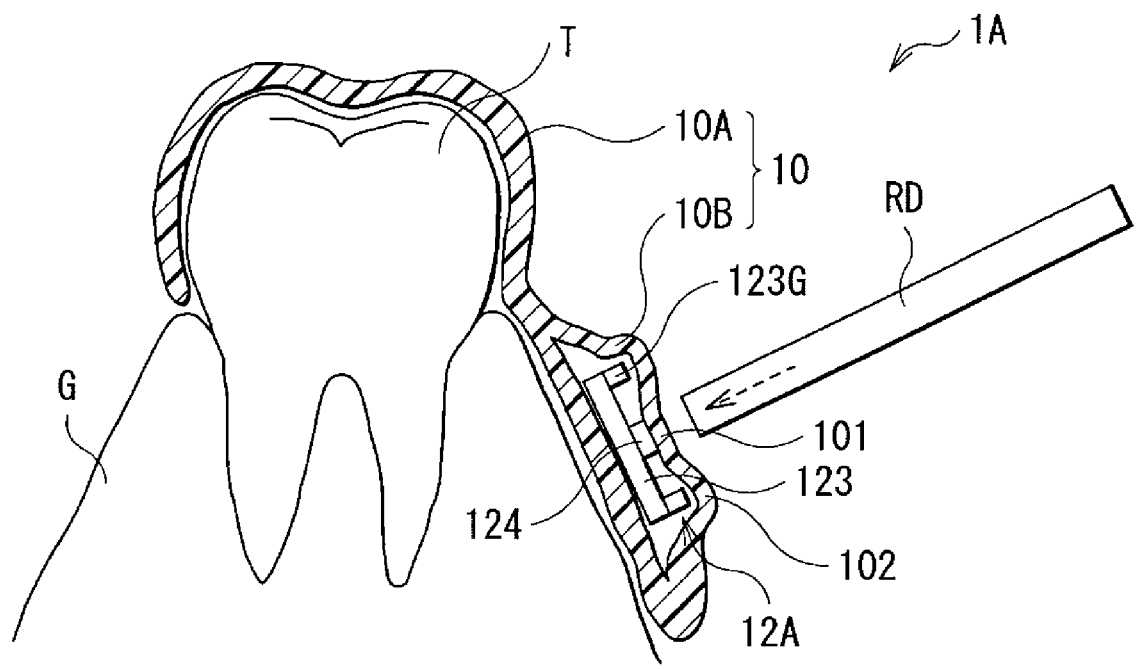
FIG. 10A is a cross-sectional view showing a schematic configuration example of a biometric information detection device as Modified Example 2 of the present disclosure.
Figure 10B:
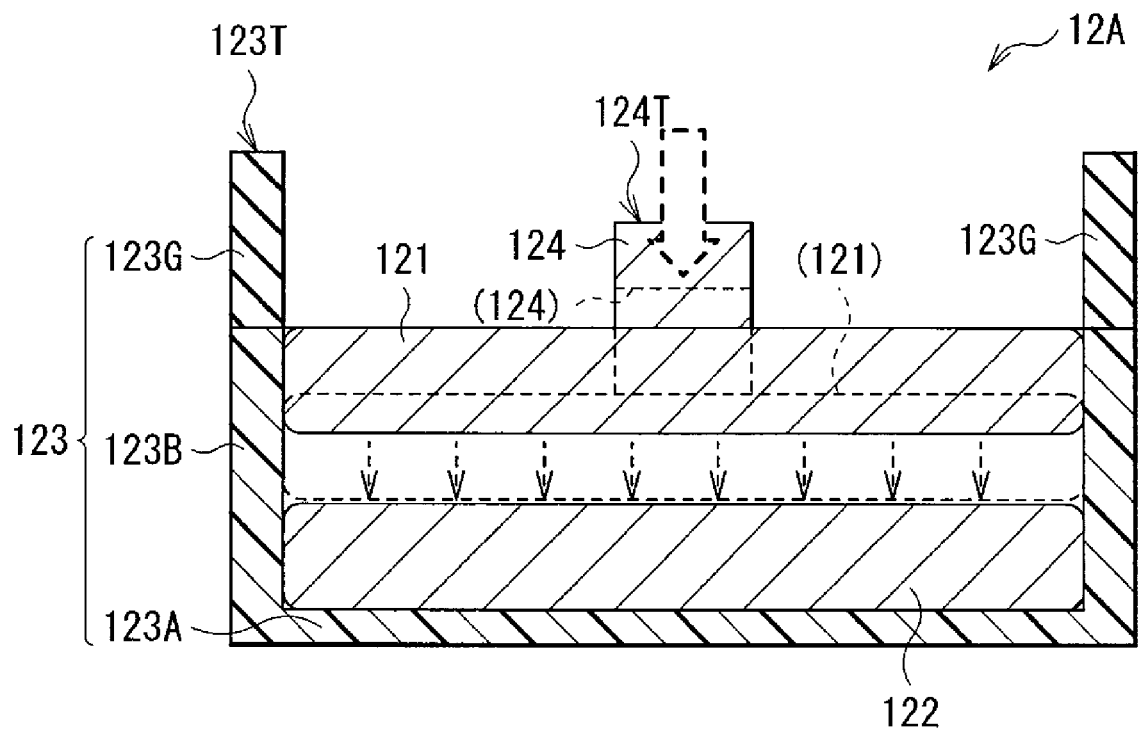
FIG. 10B is a cross-sectional view showing a schematic configuration example of a mechanical switch shown in FIG. 10A.

FIG. 10A is a cross-sectional view showing a schematic configuration of the biometric information detection device 1A as a second modified example (Modified Example 2) of the present disclosure, and corresponds to FIG. 3 showing the biometric information detection device 1 described in the above embodiment. The biometric information detection device 1A has substantially the same configuration as the biometric information detection device 1 of the above embodiment except that the mechanical switch 12A is mounted in place of the mechanical switch 12. FIG. 10B shows an enlarged cross section configuration of the mechanical switch 12A.

As shown in FIG. 10A and FIG. 10B, in the mechanical switch 12A of the biometric information detection device 1A, a protective part 123G is additionally provided in the main body 123. The protective part 123G is, for example, a wall-like part that is provided at a tip of the wall part 123B, and as shown in FIG. 10B, an upper end 123T (FIG. 10B) thereof, that is, an end on the side opposite to the bottom part 123A, protrudes from an upper end 124T of the operation unit 124 to the side opposite to the bottom part 123A. Therefore, as shown in FIG. 10A, within the shell 10, a first part 101 covering the operation unit 124 is recessed more than a second part 102 covering the periphery of the operation unit 124. In such a structure, for example, it is possible to reduce a likelihood of a subject who is wearing the biometric information detection device 1A erroneously operating the operation unit 124 of the mechanical switch 12A.

Modified Example 3

Figure 11:
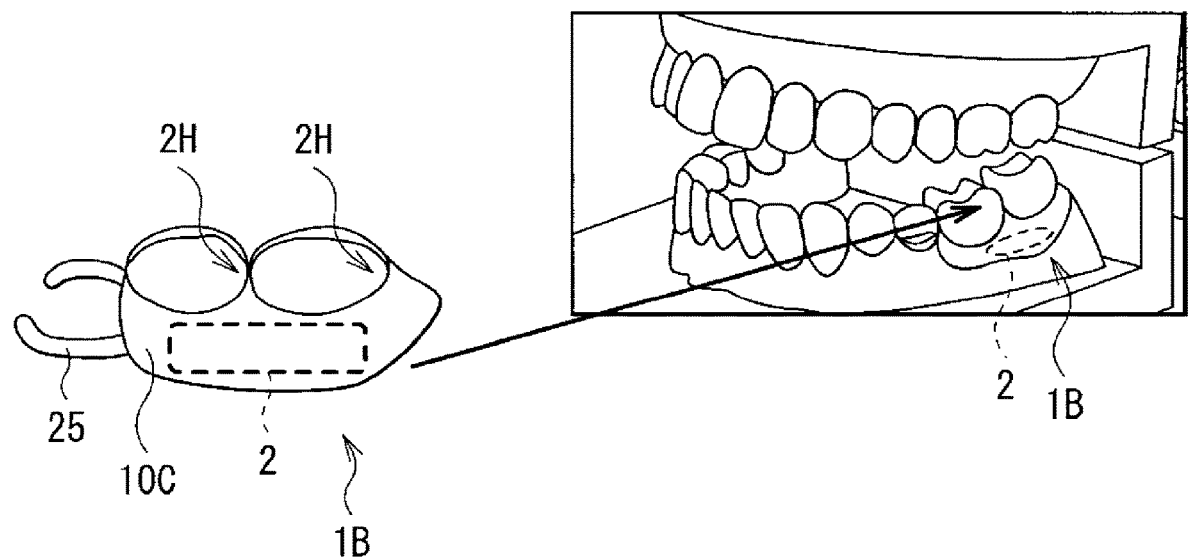
FIG. 11 is a perspective view showing an appearance and a mounting example of a biometric information detection device as Modified Example 3 of the present disclosure.

In the above embodiment, the upper part 10A as a holding member and the lower part 10B as a sealing member are integrally formed by molding using the tooth form 23. However, for example, a configuration of the biometric information detection device 1B as a third modified example (Modified Example 3) of the present disclosure shown in FIG. 11 may be used. In the biometric information detection device 1B, a holding member 25 such as a metal fitting engaging with teeth T is boned to the shell 10C in which the biometric information detection module 2 is embedded. In the shell 10C, a hole 2H into which the teeth T is inserted when it is mounted in the oral cavity is provided. The biometric information detection device 1B is produced by, for example, producing the shell 10 C according to the above vacuum forming and bonding the holding member 25 to the shell 10C.

Modified Example 4

Figure 12:
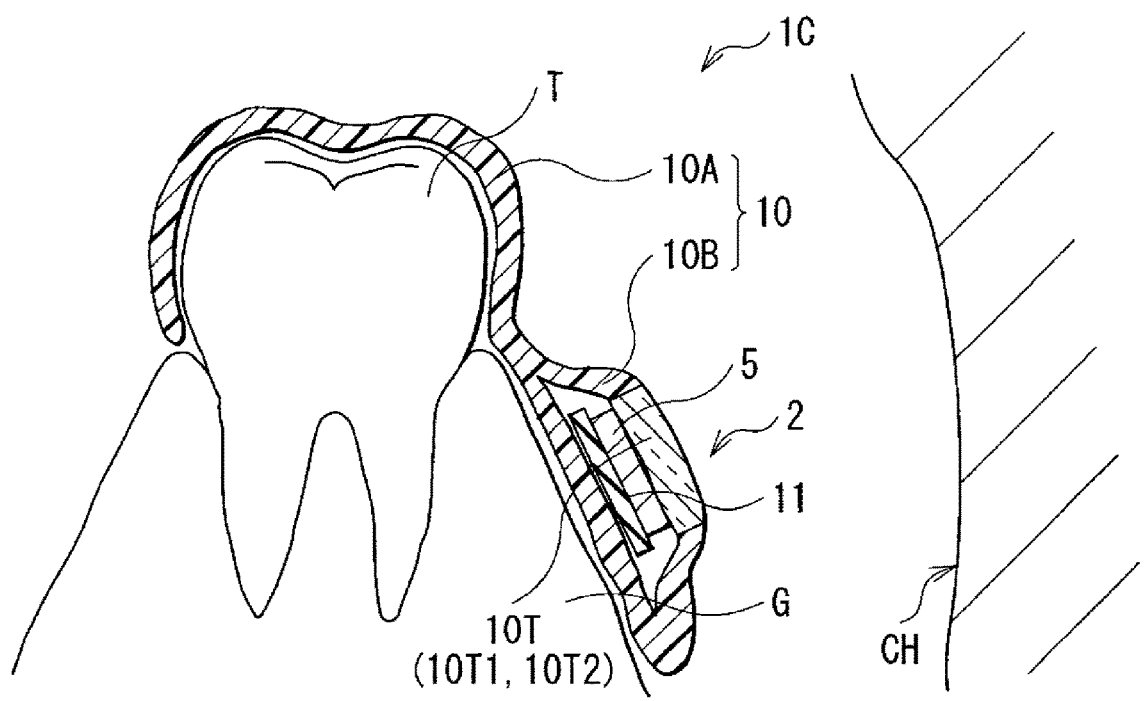
FIG. 12 is a cross-sectional view showing a schematic configuration example of a biometric information detection device as Modified Example 4 of the present disclosure.

The biometric information detection device 1 of the above embodiment emits light to the gums G, receives light reflected from the gums G, and thus detects biometric information. On the other hand, a biometric information detection device 1C of a fourth modified example (Modified Example 4) of the present disclosure shown in FIG. 12 emits light to an inner surface of a cheek CH in the oral cavity, receives light reflected from the inner surface of the cheek CH, and thus detects biometric information. In the biometric information detection device 1C, the light emitting element 5A is disposed to face the cheek CH with the first light-transmitting part 10T1 therebetween, and the light receiving element 5B is disposed near the light emitting element 5A so that it faces the cheek CH with the second light-transmitting part 10T2 therebetween. Therefore, the light-transmitting part 10T of the lower part 10B of the shell 10 covering the biometric information detection module 2 is provided on the side opposite to the gums G with the biometric information detection module 2 therebetween. Except for these points, the biometric information detection device 1C has substantially the same configuration as the biometric information detection device 1 of the above embodiment. Also in the biometric information detection device 1C, the same effects as in the biometric information detection device 1 of the above embodiment are obtained. For example, the biometric information detection device 1C of this modified example is beneficial when it is determined that a surface structure of the gums G of a subject is not favorable and it is difficult to obtain stable biometric information.

Modified Example 5

Figure 13:
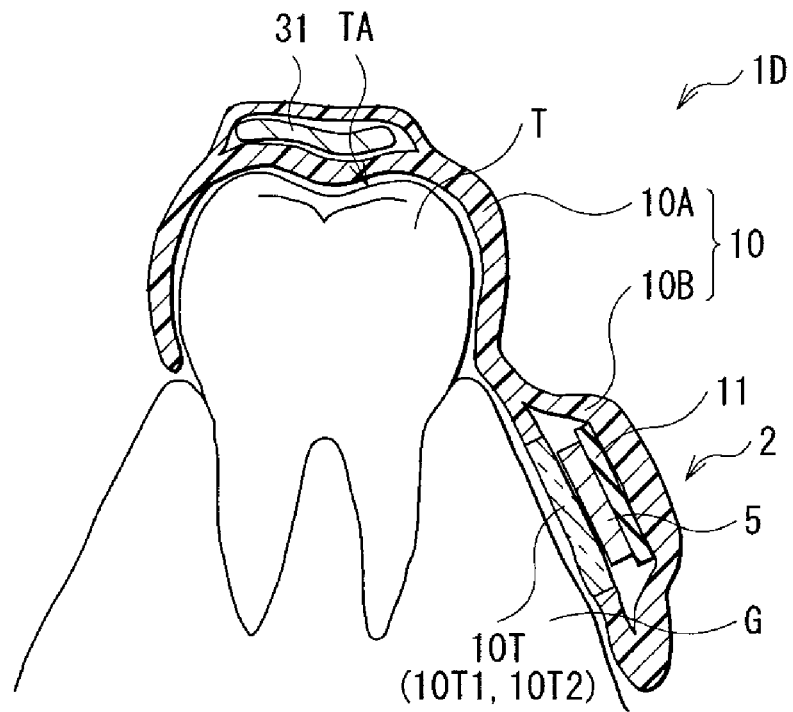
FIG. 13 is a cross-sectional view showing a schematic configuration example of a biometric information detection device as Modified Example 5 of the present disclosure.

FIG. 13 is a cross-sectional view showing a schematic configuration of a biometric information detection device 1D as a fifth modified example (Modified Example 5) of the present disclosure. In the biometric information detection device 1D, a strain sensor 31 is embedded in a part of the shell 10 covering a crown part TA of the teeth T. The strain sensor 31 is connected to the battery 6 through a power line and is connected to the signal processing unit 4 through a communication line. The strain sensor 31 receives supply of power from the battery 6 and transmits a detection signal to the signal processing unit 4. Except for these points, the biometric information detection device 1D has substantially the same configuration as the biometric information detection device 1 of the above embodiment. Therefore, also in the biometric information detection device 1D, the same effects as in the biometric information detection device 1 of the above embodiment are obtained. Moreover, when the strain sensor 31 is provided, it is possible to measure the biting strength when the teeth of the upper jaw and the teeth of the lower jaw of a subject are engaged and the pressure of the cheek or tongue of a subject in contact with the strain sensor 31. When information such as the biting strength and the pressure of the cheek and tongue is used, it is possible to obtain structural strength information and teeth alignment information necessary for artificial teeth, for example, dentures and implants. Here, as the strain sensor 31, for example, a magnetostriction sensor using magnetostriction can be applied. In addition, a pressure sensor using a piezoelectric element or the like can be applied in place of the strain sensor 31.

Modified Example 6

Figure 14:
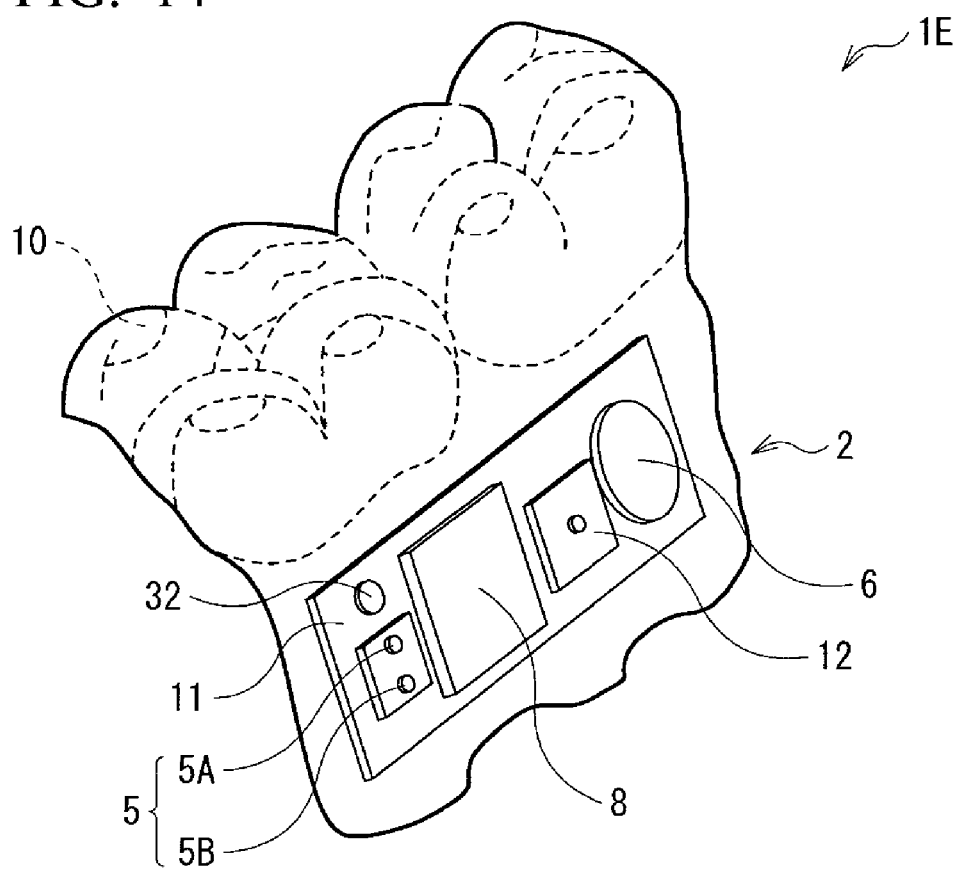
FIG. 14 is a perspective view showing a schematic configuration example of a biometric information detection device as Modified Example 6 of the present disclosure.

FIG. 14 is a perspective view showing a schematic configuration of a biometric information detection device 1E as a sixth modified example (Modified Example 6) of the present disclosure. In the biometric information detection device 1E, for example, an acceleration sensor 32 is additionally provided in the biometric information detection module 2. The acceleration sensor 32 is connected to the battery 6 through a power line and is connected to the signal processing unit 4 through a communication line. The acceleration sensor 32 receives supply of power from the battery 6 and transmits a detection signal to the signal processing unit 4. Except for these points, the biometric information detection device 1E has substantially the same configuration as the biometric information detection device 1 of the above embodiment. Therefore, also in the biometric information detection device 1E, the same effects as in the biometric information detection device 1 of the above embodiment are obtained. Then, when the acceleration sensor 32 is provided, for example, it is possible to detect a movement of the lower jaw with respect to the upper jaw of the subject. When a relative movement between the upper jaw and the lower jaw is detected, for example, it is possible to obtain structural strength information necessary for artificial teeth such as dentures and implants and this may be used for diagnosis of the presence of jaw joint abnormalities. In addition, a gyro sensor may be used in place of the acceleration sensor 32.

3. Other Modified Examples

While the present disclosure has been described above with reference to the embodiment and several modified examples, the present disclosure is not limited to the embodiment and the like, and various modifications can be made.

For example, while the biometric information detection device 1 having the shell 10 mounted so that it covers two consecutive crown parts has been exemplified in the above embodiment and the like, the biometric information detection device of the present disclosure is not limited thereto. The biometric information detection device of the present disclosure may have, for example, a shell mounted so that it covers only one crown part or a shell mounted so that it covers three or more crown parts. However, in consideration of preventing accidental ingestion, it is desirable to have a shell as large as possible. For example, it is more desirable to have a shell with a size that covers all teeth of the lower jaw or all teeth of the upper jaw.

In addition, while the biometric information detection device including one sensor has been described in the above embodiment, the biometric information detection device of the present disclosure may include two or more sensors. In addition, the biometric information detection device may be mounted on both the upper jaw and the lower jaw.

In addition, while a case in which the biometric information detection module and the biometric information detection device are installed in the oral cavity has been exemplified in the above embodiment, the biometric information detection module and the biometric information detection device of the present disclosure are not limited thereto. They may be installed in a living body outside of the oral cavity, for example, in the abdominal cavity. Alternatively, it may be attached to the outside of a living body such as the skin surface rather than the inside of a living body.

Here, effects described in this specification are only examples, and are not limited, and other effects may be provided.

In addition, the present disclosure can have the following configurations.

(1) A biometric information detection device which is configured to be installed in a living body, including: a sensor; a battery; a mechanical switch that switches between a conduction state in which power is supplied from the battery to the sensor and a cutoff state in which supply of the power is blocked; a sealing member that seals all of the sensor, the battery, and the mechanical switch; and a holding member that is configured to be attached to the living body and holds the sealing member.

(2) The biometric information detection device according to (1), wherein the mechanical switch is a self-holding type switch.

(3) The biometric information detection device according to (1) or (2), wherein the mechanical switch includes a first conductor, a second conductor, and an operation unit configured to perform a contact operation of bringing the first conductor into contact with the second conductor and a separation operation of separating the first conductor from the second conductor, and wherein, within the sealing member, a first part covering the operation unit is recessed more than a second part covering the periphery of the operation unit.

(4) The biometric information detection device according to (1) or (2), wherein the battery has an electrode structure; and an exterior member which includes a main body area covering the electrode structure and a sealing area protruding from the main body area, and in which the electrode structure is enclosed, and wherein the sealing area of the exterior member surrounds at least a part of the mechanical switch.

(5) The biometric information detection device according to (4), wherein the mechanical switch includes: a first conductor, a second conductor, and an operation unit configured to perform a contact operation of bringing the first conductor into contact with the second conductor and a separation operation of separating the first conductor from the second conductor, and is provided in the main body area or the sealing area of the exterior member, wherein the sealing area of the exterior member has an eaves part positioned on the side opposite to the main body area of the exterior member in a view from the operation unit, and wherein the eaves part has an opening or a notch provided at a position corresponding to the operation unit.

(6) The biometric information detection device according to any one of (1) to (5), wherein the sensor includes a light emitting element that is able to emit light and a light receiving element that is able to receive the light emitted from the light emitting element, and wherein the sealing member includes a first light-transmitting part that covers the light emitting element and is able to transmit the light and a second light-transmitting part that covers the light receiving element and is able to transmit the light.

(7) The biometric information detection device according to (6), wherein the light emitting element is configured to be disposed to face the gums in the living body with the first light-transmitting part therebetween, and wherein the light receiving element is disposed to face the gums in the living body with the second light-transmitting part therebetween.

(8) The biometric information detection device according to (6), wherein the light emitting element is configured to be disposed to face an inner surface of the cheek with the first light-transmitting part therebetween, and wherein the light receiving element is disposed to face an inner surface of the cheek with the second light-transmitting part therebetween.

(9) The biometric information detection device according to any one of (6) to (8), wherein the light has a wavelength of 400 nm or more and 1,000 nm or less.

(10) The biometric information detection device according to any one of (6) to (9), further including a signal processing unit that is sealed with the sealing member, receives supply of power from the battery, and generates a data signal based on an output signal from the sensor, and a transmitting and receiving unit that is sealed with the sealing member and receives supply of power from the battery, is able to transmit the data signal from the signal processing unit to an external device, and is able to receive a control signal from the external device.

(11) The biometric information detection device according to any one of (6) to (10), wherein the first light-transmitting part and the second light-transmitting part are formed of a thermoplastic polymer compound.

(12) The biometric information detection device according to any one of (1) to (11), wherein the sensor is a pulse wave sensor, a pulse oximeter or a glucose sensor.

(13) The biometric information detection device according to any one of (1) to (12), wherein the holding member and the sealing member are an integrally formed mouthpiece.

(14) The biometric information detection device according to any one of (1) to (13), further including
another sensor configured to measure a physical quantity.

(15) A biometric information detection module including: a sensor; a battery; a mechanical switch that switches between a conduction state in which power is supplied from the battery to the sensor and a cutoff state in which supply of the power is blocked; and a sealing member that seals all of the sensor, the battery, and the mechanical switch.

(16) A method of producing a biometric information detection device installed in a living body, including: preparing a sensor, a battery, and a mechanical switch that switches between a conduction state in which power is supplied from the battery to the sensor and a cutoff state in which supply of the power is blocked; inserting the sensor, the battery and the mechanical switch between a pair of sealing films, then heating and molding the pair of sealing films, and thereby forming a sealing member with which the sensor, the battery, and the mechanical switch are sealed; and forming a holding member that is configured to be attached to the living body and holds the sealing member.

(17) The method of producing a biometric information detection device according to (16), wherein the sealing member and the holding member are integrally formed by the molding.

(18) A method of producing a biometric information detection module, including: preparing a sensor, a battery, and a mechanical switch that switches between a conduction state in which power is supplied from the battery to the sensor and a cutoff state in which supply of the power is blocked; and inserting the sensor, the battery and the mechanical switch between a pair of sealing films, then heating and molding the pair of sealing films, and thereby forming a sealing member with which the sensor, the battery, and the mechanical switch are sealed.

REFERENCE NUMERALS 1, 1A to 1C Biometric information detection device
2 Biometric information detection module
2H Hole
3 Transmitting and receiving unit
4 Signal processing unit
5 Light sensor
6 Battery
7 Network connector
8 Transmitting and receiving module
9A, 9B Sealing film
10 Shell
11 Mounting board
12, 12A Mechanical switch
121 First conductor
122 Second conductor
123 Main body
123A Bottom part
123B Wall part
123G Protective part
124 Operation unit 13 Battery
131 Electrode structure
132 Exterior member
23 Tooth form
24 Heater
31 Strain sensor
32 Acceleration sensor
G Gum
T Teeth
RD Operation rod

What is claimed is:

1. A biometric information detection device which is configured to be installed in an oral cavity, comprising:
   a sensor;
   a battery;
   a mechanical switch that switches between a conduction state in which power is supplied from the battery to the sensor and a cutoff state in which supply of the power is blocked;
   a sealing member that seals all of the sensor, the battery, and the mechanical switch, and is configured to cover gums in the oral cavity; and
   a holding member that is configured to be attached to teeth in the oral cavity, and holds the sealing member, wherein
   the mechanical switch includes an operation unit that is sealed within the sealing member at a position on an opposite side of at least a portion of the sealing member to the gums to accept a pushing operation.

2. The biometric information detection device according to claim 1,
   wherein the mechanical switch is a self-holding type switch.

3. The biometric information detection device according to claim 1,
   wherein the mechanical switch further includes a first conductor, and a second conductor,
   wherein the operation unit is configured to perform a contact operation of bringing the first conductor into contact with the second conductor and a separation operation of separating the first conductor from the second conductor, and
   wherein, within the sealing member, a first part covering the operation unit is recessed more than a second part covering the periphery of the operation unit.

4. The biometric information detection device according to claim 1,
   wherein the battery has an electrode structure; and an exterior member which includes a main body area covering the electrode structure and a sealing area protruding from the main body area, and in which the electrode structure is enclosed, and
   wherein the sealing area of the exterior member surrounds at least a part of the mechanical switch.

5. The biometric information detection device according to claim 4,
   wherein the mechanical switch further includes a first conductor, and a second conductor,
   wherein the operation unit is configured to perform a contact operation of bringing the first conductor into contact with the second conductor and a separation operation of separating the first conductor from the second conductor, and is provided in the main body area or the sealing area of the exterior member,
   wherein the sealing area of the exterior member has an eaves part positioned on the side opposite to the main body area of the exterior member in a view from the operation unit, and
   wherein the eaves part has an opening or a notch provided at a position corresponding to the operation unit.

6. The biometric information detection device according to claim 1,
   wherein the sensor includes a light emitting element that is able to emit light and a light receiving element that is able to receive the light emitted from the light emitting element, and
   wherein the sealing member includes a first light-transmitting part that covers the light emitting element and is able to transmit the light, and a second light-transmitting part that covers the light receiving element and is able to transmit the light.

7. The biometric information detection device according to claim 6,
   wherein the light emitting element is configured to be disposed to face the gums in the oral cavity with the first light-transmitting part therebetween, and
   wherein the light receiving element is disposed to face the gums in the oral cavity with the second light-transmitting part therebetween.

8. The biometric information detection device according to claim 6,
   wherein the light emitting element is configured to be disposed to face an inner surface of a cheek in the oral cavity with the first light-transmitting part therebetween, and
   wherein the light receiving element is configured to be disposed to face an inner surface of the cheek with the second light-transmitting part therebetween.

9. The biometric information detection device according to claim 6,
   wherein the light has a wavelength of 400 nm or more and 1,000 nm or less.

10. The biometric information detection device according to claim 6, further comprising
    a signal processing unit that is sealed with the sealing member, receives supply of power from the battery, and generates a data signal based on an output signal from the sensor, and
    a transmitting and receiving unit that is sealed with the sealing member and receives supply of power from the battery, is able to transmit the data signal from the signal processing unit to an external device, and is able to receive a control signal from the external device.

11. The biometric information detection device according to claim 6,
    wherein the first light-transmitting part and the second light-transmitting part are formed of a thermoplastic polymer compound.

12. The biometric information detection device according to claim 1,
    wherein the sensor is a pulse wave sensor, a pulse oximeter or a glucose sensor.

13. The biometric information detection device according to claim 1,
    wherein the holding member and the sealing member are an integrally formed mouthpiece.

14. The biometric information detection device according to claim 1, further comprising
    another sensor configured to measure a physical quantity.

15. A method of producing a biometric information detection device according to claim 1, the method comprising:

preparing the sensor, the battery, and the mechanical switch;

inserting the sensor, the battery and the mechanical switch between a pair of sealing films, then heating and molding the pair of sealing films, and thereby forming a sealing member with which the sensor, the battery, and the mechanical switch are sealed; and forming the holding member.

16. The method of producing a biometric information detection device according to claim 15, wherein the sealing member and the holding member are integrally formed by the molding.

17. The biometric information detection device according to claim 1, wherein the mechanical switch is configured to accept the pushing operation in a direction toward the gums.

* * * * *